United States Patent [19]

Singleton

[11] 4,240,436
[45] Dec. 23, 1980

[54] THERAPEUTIC COLD PACK

[76] Inventor: Rosa R. Singleton, 3106 Edgewood Ave., Richmond, Va. 23222

[21] Appl. No.: 938,336

[22] Filed: Aug. 31, 1978

[51] Int. Cl.³ .............................................. A61F 7/00
[52] U.S. Cl. .................................. 128/403; 128/341; 128/401
[58] Field of Search ............... 128/399, 401, 402, 403, 128/24.1, 79, 98, 82.1, 168, 275.1, 294, 295, 303.12, 344, 343, 341, 342

[56] References Cited

U.S. PATENT DOCUMENTS

| | | | |
|---|---|---|---|
| 734,213 | 7/1903 | Barnes | 128/402 |
| 969,134 | 8/1910 | Cowie | 128/343 |
| 2,249,298 | 7/1941 | Ratti | 128/344 |
| 2,378,087 | 6/1945 | Kearney | 128/399 |
| 2,512,185 | 5/1970 | Ellis | 128/295 |
| 2,562,121 | 7/1951 | Poux | 128/402 |
| 3,175,558 | 3/1965 | Caillouette et al. | 128/403 |
| 3,780,537 | 12/1973 | Spencer | 128/399 |

FOREIGN PATENT DOCUMENTS

| | | | |
|---|---|---|---|
| 336941 | 4/1959 | Switzerland | 128/79 |
| 1011517 | 12/1965 | United Kingdom | 128/295 |

Primary Examiner—Robert W. Michell
Assistant Examiner—Arthur S. Rose
Attorney, Agent, or Firm—Lawrence Harbin

[57] ABSTRACT

A disposable perineal ice pack having an anatomical shape specially adapted for treatment of swelling and other disfunction of the rectal-vaginal pelvis region of female subjects, composed of a flexible hollow synthetic material having a cold temperature storage medium therein, such as water, or other liquid freezable between zero and thirty-two degrees Fahrenheit, wherein said ice pack is specially contoured to compliment both the rectal and vaginal regions adaptable for use during post-operative surgeries or traumatic insults to the pelvic region.

4 Claims, 6 Drawing Figures

THERAPEUTIC COLD PACK

BACKGROUND OF THE INVENTION

This invention relates to a therapeutic ice packs adapted for the reduction of swelling and the relief of pain resulting from soft tissue surgery or traumatic insults. Particularly, the inventin concerns ice packs having special shapes adaptable to be used in special circumstances. As used herein, ice packs include cold packs of every nature, not necessarily being limited to bags or bottles having water or ice as its cold temperature storage medium. Other types of liquid or solid medium are also of concern.

It should be noted at the outset, that the use of ice packs as aforestated is not novel and has been widely used within the medical field for therapeutic treatment of swelling and for the reduction of pain resulting from traumatic injuries or surgery. The effect of reduction of temperature in an area of traumatic insult facilitates the reduction in extravasatin of fluids from the intracellular compartment into the interstitial areas which causes swelling. Ice packs have proven to be convenient and effective in reducing swelling locally. The application of ice packs in a localized area reduces pressure at the injured site and thereby substantially reduces pain within the first six to twelve hours after injury or operation. Also, ice packs will aid in the constriction and the maintenance thereof of capillary vessels to retard or cease bleeding resulting from severed vessels.

Ice packs are generally composed of flexible material such as rubber, which contain a freezable medium therein. The freezable medium may be water or a pliable slurry both of which serves as a cold temperature storage means. In that regard, inventor has noted several patents, one of which is U.S. Pat. No. 2,697,424 issued to Hanna on Dec. 21, 1954 wherein a thereapeutic cold pack is disclosed having a particular pliable slurry contained therein, such as a mixture 10% isopropyl alcohol and water which freezes near 20 degrees Fahrenheit.

Regarding ice packs having special anatomical shapes, such as that which this invention is concerned, the inventor has noted U.S. Pat. No. 734,213 issued to Barnes on July 21, 1903. The Barnes patent discoses a hot water bag, which may serve the purpose of an ice pack, consisting of flexible material, having a rectal insert thereon, adapted to worn in the pelvis region. Unlike the instant invention, the device disclosed by the Barnes patent is not disposable. The inventor also notes a disposable hemorrhoidal device having a cold temperature storage medium for therapeutic treatment of hemorrhoids in U.S. Pat. No. 3,939,842 issued to Harris on Feb. 24, 1976.

Disposability of various therapeutic surgical devices and aids are extremely desirable in both hospitals and private offices of physicians. Not only do features of disposability eliminates the possibility of communicating diseases, germs, bacteria, etc, but it reduces labor required for cleaning and disenfecting the devices and surgical aids. Of course, the effects of non-recyckable goods on the ecology must be weighted in light of benefits achieved otherwise.

There exists several other types of special purpose ice packs, none of which anticipates the instant invention, which will be more fully hereinafter described in the following specification and appended drawings.

In view of the foregoing, it is the intent of the inventor herein to provide a disposable perineal ice pack specially contoured and anatomically shaped to compliment the rectal and vaginal regions of female subjects, particularly in the interest of convenience and sanitation, to therapeutically treat swelling and/or minimize external hemorrage and/or minimizing pain associated with surgical operations or traumatic insults to the rectal and vaginal regions.

It is, of course, another object of the invention to perform the aforestated objective in the most economical and efficient manner.

Further and additional objects of the invention will become readily apparent upon presentation of the foregoing detailed description.

SUMMARY OF THE INVENTION

The invention consists of a disposable perineal ice pack having an anatomical shape and is composed of a flexible material, such as polyethylene, having contained therein a cold temperature storage means, such as water or a chemical slurry, the novel and unique features thereof residing in its shape, particularly, its anatomical shape adapted to be complimentary to the rectal-vaginal pelvis region of female subjects.

The structure is essentially elongated having relative width and thickness and opposed ends and opposed surfaces. The width of the respective ends compliment the width of the respective portions of the pelvis region and is contoured from a relatively wide width at the end associated with the vaginal area and is tapered to a relatively narrower width at the end associated with the rectal region. One side of the structure is adapted to be in intimate contact with the rectal vaginal tissue, and has disposed therein, a lengthwise raised contour adapted for partial insertion into the vaginal crevice, and in another embodiment of the invention, there is also disposed a rectal insert protruding from the raised contour adapted to be inserted into the rectal orifice.

The ice pack structure may be adapted to be a hermetically sealed device having permanently contained therein a cold temperature storage medium, or the structure may have an orifice thereon, with a removable cap, for the infusion of the cold storage means.

The entire structure is generally refrigerated prior to use, and is discarded after use.

A more detailed description and presentation of the invention is now presented.

BRIEF DESCRIPTION OF THE INVENTION

Figure 1:
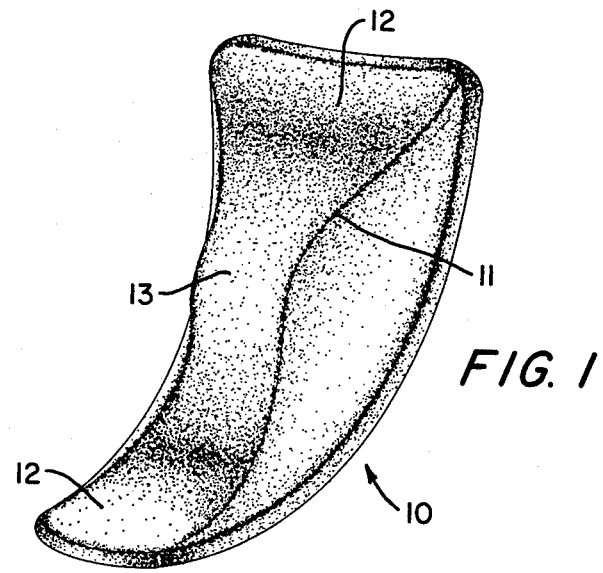
FIG. 1 discloses a three dimensional view of one embodiment of the invention.
Figure 2:
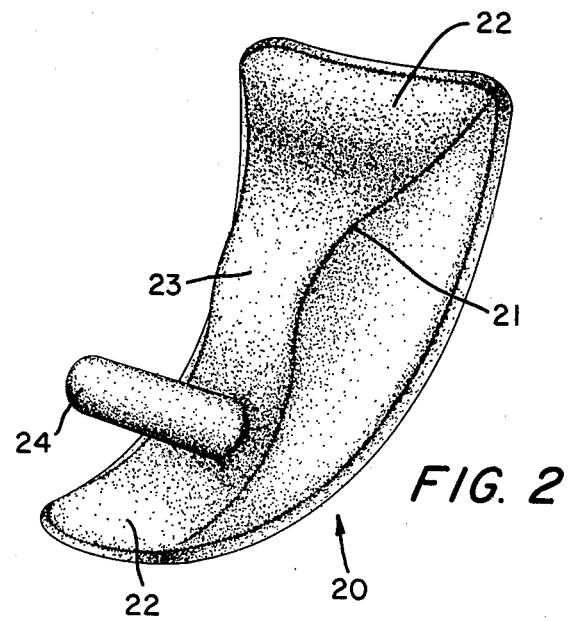
FIG. 2 discloses a three dimensional view of a second embodiment of the invention.

Referring to the drawings, FIGS. 1 and 2 discloses two embodiments of the invention, the difference being the addition of the rectal insert associated with FIG. 2.

Referring particularly to FIG. 1, an ice pack structure 10 is disclosed having a generally anatomically shape, wherein an elongated raised contoured portion is generally shown by surface 13. It should be understood that surface 12 is also anatomically designed to compliment the surface portions of the vaginal and rectal areas of female subjects.

Figure 3A:
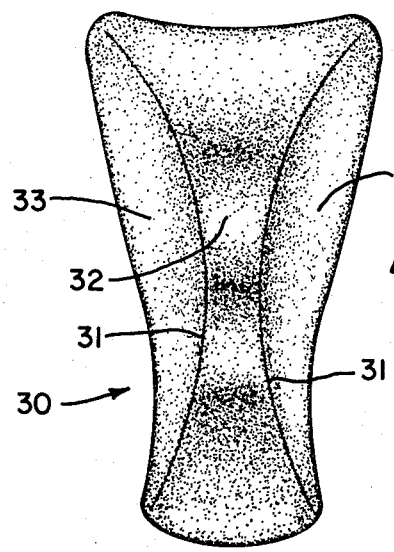
FIGS. 3(a) and 3(b) show the respective front and side view of the embodiment of the invention generally disclosed in FIG. 1.
Figure 3B:
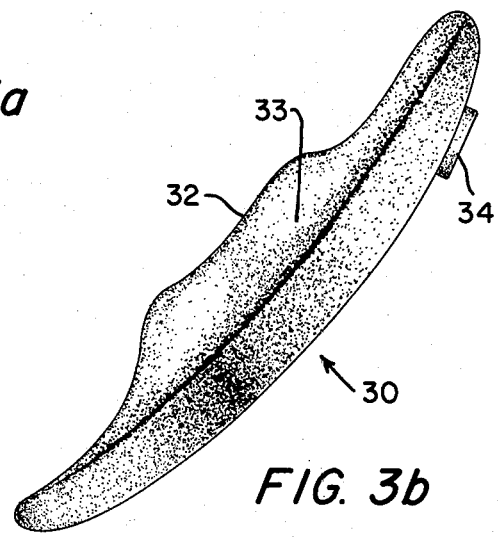

A more detailed version of the ice pack structure 10 is disclosed in FIGS. 3(a) and 3(b), wherein a respective front and side views are shown. Structure 30 of FIG. 3(a) discloses generally the lengthwise raised contour 32, disposed on the anatomical surface 33. It is noted that the width of the raised contour 32 generally varies in order to anatomically compliment the area of application as aforestated. FIG. 3(b) discloses a side view of structure 30 wherein surface 32 is shown to be anatomically complimentary.

Figure 4A:
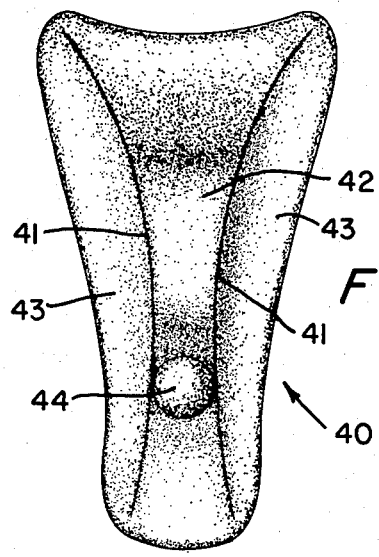
FIGS. 4(a) and 4(b) show the respective front and side views of the embodiment of the invention disclosed in FIG. 2.
Figure 4B:
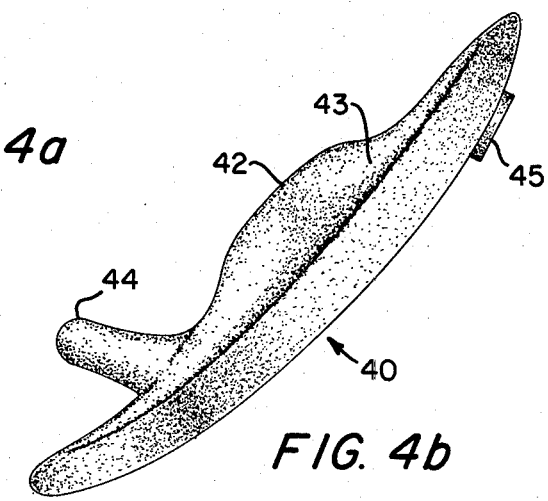

Now, referring to FIGS. 4(a) and 4(b), a similar structure is shown, however, an additional rectal insert 44 is shown to be disposed on the anatomical surface 33. Raised contoured portion 42 and rectal insert 44 are adapted to compliment the vaginal and rectal areas respectively. The entire structure is generally contoured in shape to approximate the average or mean curvature of the pelvis region.

Additionally, the material from which the structure is composed may be flexible to facilitate its effectiveness and enhance comfort during use. The structures are hollow and may be preformed with cold temperature storage medium contained therein, or, the structure may contain an orifice, indicated at elements 34 and 45 of FIGS. 3(b) and 4(b) respectively. The orifice contain removable cap 34 and 35 for the placement of a cold storage medium within said structure.

The cold temperature storage medium may consist of water or other chemical slurries which has a freezing point between zero and 32 degrees Fahrenheit. As previously indicated, a slurry which may be employed is a mixture of 10% isopropyl alcohol and water which creates a semi-pliable slurry at a temperature of 20 degrees Fahrenheit. Other chemical inert slurries may be employed hich is non-reactive to the structure and soft tissue.

The materials from which the structure may be composed include polyethylene, rubber, plastic or other synthetic or natural materials.

It should be noted that other variations, adaptations, or arrangements may be instituted by persons skilled in the art to which this subject matter petains, but however, it is not the intent of the inventor to limit the scope of the invention to what exactly has been shown, described, or presented, but to include all arrangements, adaptations and modifications which may be made regarding the design, cold storage medium and material.

Now, therefore, a complete description of the invention having been made, what is claimed is:

1. A disposable cold pack having a preformed anatomical shape for treatment of the vaginal and rectal regions comprising:

A hollow anatomically-shaped cold storage pack that includes a cold storage medium, said cold storage pack being a unitary structure that completely encapsulates therein said cold storage medium, the combination of said cold storage pack and said cold storage medium being preformed such that it fits against said vaginal and rectal regions without requiring manipulation of said cold pack, an elongated base having a vaginal end and a rectal end, and two side edges, said base being preformed with a curve along its length and said curve generally conforming to the curve of the perineal area from the vaginal region to the rectal region, said rectal end being relatively narrower than said vaginal end, said two edges being concave and extending between said vaginal and rectal ends, said edges converging from said vaginal end inwardly towards said relatively narrower rectal end thereby being complementary to and readily conforming to the shape of the vaginal and rectal regions, first and second side portions extending upwardly from said side edges of said base and angled towards one another, and an elongated upward contacting surface extending from said vaginal end to said rectal end of said base and connecting the upper edges of said first and second side portions to form an enclosure, said contacting surface having side edges extending from said vaginal end to said rectal end of said base, said side edges being generally concave and curved inwardly towards one another, said first and second side portions being generally concave and inwardly curved towards said contacting surface thereby to readily conform to and complement the shape of the vaginal and rectal regions when in contact therewith, said contacting surface including at the mid-portion thereof a lengthwise elongated and outwardly protruding raised surface portion partially extending along said elongated structure, said raised surface portion being adapted for partial insertion into both said vaginal and rectal openings.

2. The therapeutic cold storage pack as recited in claim 1 further including an integrally formed rectal insert comprising an elongated tubular member disposed on said outwardly protruding raised surface portion near the rectal end of said cold storage pack, said tubular member extending angularly from the curved surface of said contact surface and adapted for being inserted into the rectal opening when said cold storage pack is applied in intimate contact with said vaginal and rectal area.

3. The invention of claim 1 or 2 wherein said cold storage medium comprises a slurry including a mixture of water and alcohol.

4. The invention of claim 1 or 2 wherein said thereapeutic cold pack is composed of polyethylene.

* * * * *